(12) United States Patent
Akagane

(10) Patent No.: US 12,059,824 B2
(45) Date of Patent: Aug. 13, 2024

(54) METHOD OF MANUFACTURING ULTRASOUND PROBE, METHOD OF MANUFACTURING AN ULTRASOUND TREATMENT TOOL, AND ULTRASOUND TREATMENT TOOL

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1035 days.

(21) Appl. No.: 16/993,412

(22) Filed: Aug. 14, 2020

(65) Prior Publication Data

US 2020/0368943 A1   Nov. 26, 2020

Related U.S. Application Data

(63) Continuation of application No. PCT/JP2018/007636, filed on Feb. 28, 2018.

(51) Int. Cl.
*A61B 5/00* (2006.01)
*A61B 17/32* (2006.01)
(Continued)

(52) U.S. Cl.
CPC .. *B29C 37/0028* (2013.01); *A61B 17/320092* (2013.01); *B29C 45/14008* (2013.01); *A61B 2017/00526* (2013.01); *B29C 2037/0035* (2013.01); *B29K 2071/00* (2013.01); *B29K 2509/08* (2013.01); *B29K 2509/10* (2013.01); *B29L 2031/7546* (2013.01)

(58) Field of Classification Search
CPC .......... B29C 37/0028; B29C 45/14008; B29C 2037/0035; B29K 2509/08; B29K 2071/00
See application file for complete search history.

(56) References Cited

U.S. PATENT DOCUMENTS

2006/0071580 A1\* 4/2006 Sawada ............ B06B 1/067
310/369
2008/0220176 A1\* 9/2008 Carlblom ............ C08F 2/22
523/334
(Continued)

FOREIGN PATENT DOCUMENTS

WO 2006/109383 A1 10/2006
WO 2015/020147 A1 2/2015
(Continued)

OTHER PUBLICATIONS

Apr. 17, 2018 International Search Report issued in International Patent Application No. PCT/JP2018/007636.

*Primary Examiner* — Joel F Brutus
(74) *Attorney, Agent, or Firm* — Oliff PLC

(57) ABSTRACT

A method of manufacturing an ultrasound probe includes: forming a probe body; forming a coating portion by applying a liquid containing a resin component as a main component and a filler to a predetermined region on an outer surface of the probe body and heating the liquid; and forming a mold portion by placing the probe body on which the coating portion is formed in a die and pouring a resin containing a same component as the resin component serving as the main component of the coating portion in the die.

10 Claims, 7 Drawing Sheets

(51) Int. Cl.
  *B29C 37/00*   (2006.01)
  *B29C 45/14*   (2006.01)
  *A61B 17/00*   (2006.01)
  *B29K 71/00*   (2006.01)
  *B29K 509/08*   (2006.01)
  *B29K 509/10*   (2006.01)
  *B29L 31/00*   (2006.01)

(56) References Cited

U.S. PATENT DOCUMENTS

| | | |
|---|---|---|
| 2008/0234710 A1 | 9/2008 | Neurohr et al. |
| 2009/0020870 A1 | 1/2009 | Watanabe et al. |
| 2013/0301114 A1* | 11/2013 | Sangawa .............. A61B 5/0097 |
| | | 359/305 |
| 2015/0148680 A1* | 5/2015 | Hirayama ............ A61B 8/4444 |
| | | 600/459 |
| 2016/0144204 A1 | 5/2016 | Akagane |
| 2016/0374744 A1 | 12/2016 | Akagane |
| 2018/0116688 A1 | 5/2018 | Akagane |

FOREIGN PATENT DOCUMENTS

| | | |
|---|---|---|
| WO | 2016/194568 A1 | 12/2016 |
| WO | 2017/002456 A1 | 1/2017 |

\* cited by examiner

METHOD OF MANUFACTURING ULTRASOUND PROBE, METHOD OF MANUFACTURING AN ULTRASOUND TREATMENT TOOL, AND ULTRASOUND TREATMENT TOOL

CROSS-REFERENCE TO RELATED APPLICATION

This application is a continuation of International Application No. PCT/JP2018/007636, filed on Feb. 28, 2018, the entire contents of which are incorporated herein by reference.

BACKGROUND

In the related art, there is known an ultrasound treatment tool that applies ultrasound energy to a site (hereinafter, referred to as a target site) to be joined and incised in a biological tissue to incise the target site while joining the target site.

The ultrasound treatment tool includes an ultrasound probe that treats the target site by applying ultrasound vibration to the target site.

However, when the target site is treated by applying the ultrasound energy, a temperature of an outer surface other than the treatment surface in the ultrasound probe also rises. Then, when the outer surface comes into contact with a site other than the target site in the biological tissue in a state in which the temperature of the outer surface is high, an unintended action is exerted on the biological tissue.

SUMMARY

The present disclosure relates to a method of manufacturing an ultrasound probe, a method of manufacturing an ultrasound treatment tool, and an ultrasound treatment tool.

In some embodiments, a method of manufacturing an ultrasound probe includes: forming a probe body; forming a coating portion by applying a liquid containing a resin component as a main component and a filler to a predetermined region on an outer surface of the probe body and heating the liquid; and forming a mold portion by placing the probe body on which the coating portion is formed in a die and pouring a resin containing a same component as the resin component serving as the main component of the coating portion in the die.

In some embodiments, a method of manufacturing an ultrasound treatment tool includes: forming a probe body having a treatment portion provided on a distal end of the probe body; forming a coating portion by applying a liquid containing a resin component as a main component and a filler to a predetermined region on an outer surface of the probe body and heating the liquid; forming a mold portion by placing the probe body in which the coating portion is formed in a die and pouring a resin containing a same component as the resin component serving as the main component of the coating portion in the die; and assembling the probe body provided with the mold portion on a handle that can be operated by an operator.

In some embodiments, an ultrasound treatment tool includes: an ultrasound transducer configured to generate ultrasound vibration; a probe body including a proximal end to which the ultrasound transducer is connected and a distal end on which a treatment portion is provided, the probe body being configured to transmit the ultrasound vibration from the proximal end to the distal end, and treat a biological tissue by applying the ultrasound vibration from the treatment portion to the biological tissue; a jaw configured to hold the biological tissue between the jaw and the treatment portion; a coating portion that is provided on a non-treatment surface of the probe body, the coating portion containing a mica as a filler in a resin serving as a main component; and a mold portion that contains a glass filler in the resin serving as a same main component as the coating portion, and is formed on the coating portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
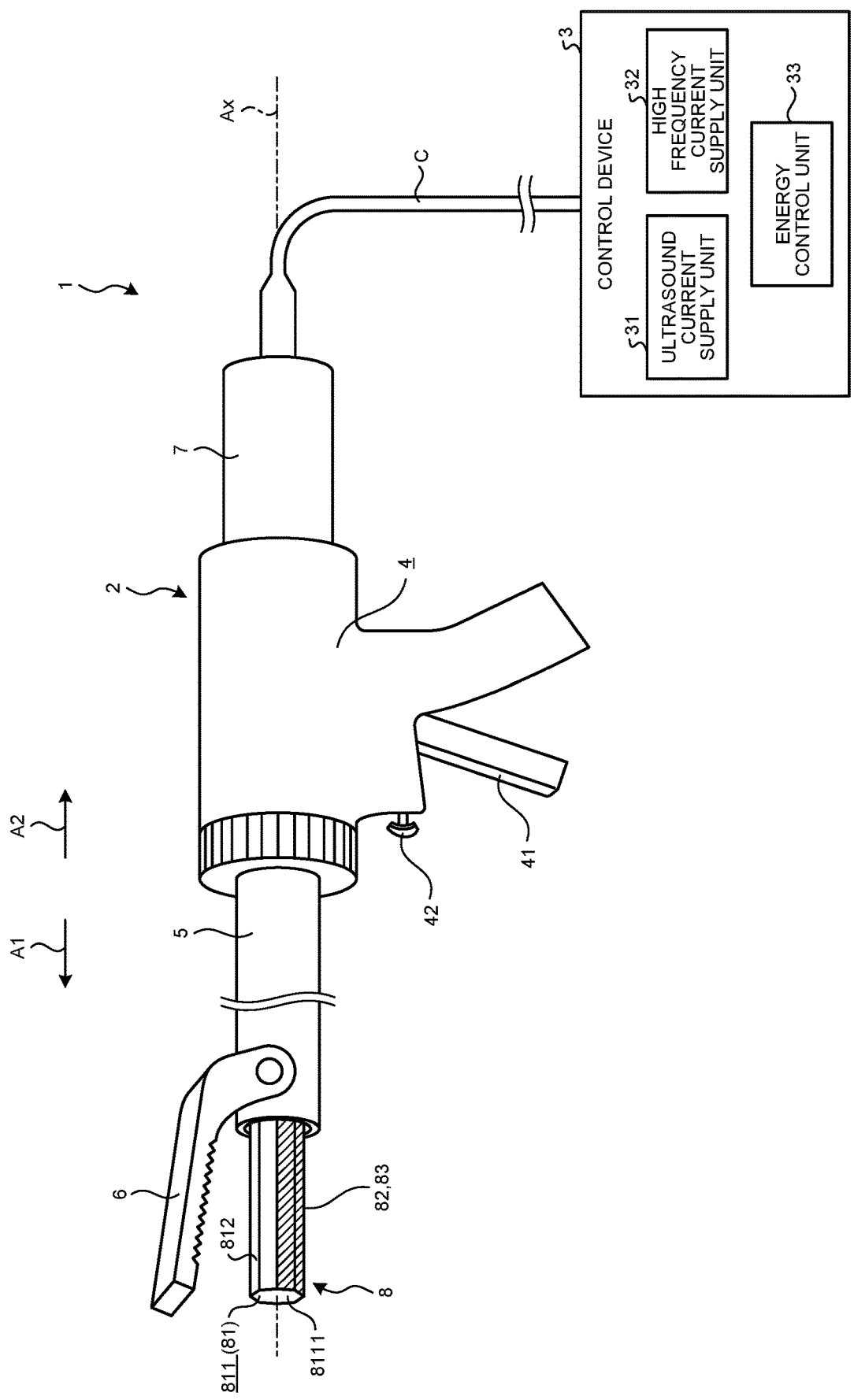
FIG. 1 is a diagram illustrating a treatment apparatus according to an exemplary embodiment.

Hereinafter, a mode (hereinafter, "embodiment") for carrying out the disclosure will be described with reference to the accompanying drawings. Note that the disclosure is not limited to embodiments described below. Further, in the description of the drawings, the same reference numerals refer to the same parts.

Schematic Configuration of Treatment Apparatus

FIG. 1 is a diagram illustrating a treatment apparatus 1 according to an exemplary embodiment.

The treatment apparatus 1 applies ultrasound energy and high frequency energy to a site (hereinafter, referred to as target site) to be treated in a biological tissue, thereby treating the target site. Here, the treatment means, for example, coagulation and incision of the target site. As illustrated in FIG. 1, the treatment apparatus 1 includes an ultrasound treatment tool 2 and a control device 3.

The ultrasound treatment tool 2 is, for example, a medical treatment tool that uses a BLT (bolt-clamped Langevin type transducer) for treating the target site while passing through an abdominal wall. As illustrated in FIG. 1, the ultrasound treatment tool 2 includes a handle 4, a sheath 5, a jaw 6, a transducer unit 7, and an ultrasound probe 8.

The handle 4 is a portion that an operator holds by hand. The handle 4 is provided with an operation knob 41 and an operation button 42 as illustrated in FIG. 1.

The sheath 5 has a cylindrical shape. In the following, a central axis of the sheath 5 will be referred to as a central axis Ax (FIG. 1). In the following, one side along the central axis Ax will be referred to as distal end side A1 (FIG. 1), and the other side will be referred to as proximal end side A2 (FIG. 1). The sheath 5 is attached to the handle 4 by inserting a part of the proximal end side A2 into the handle 4 from the distal end side A1 of the handle 4.

The jaw 6 is rotatably attached to the end portion of the distal end side A1 in the sheath 5 and holds a target site between the jaw 6 and a portion of the distal end side A1 of the ultrasound probe 8. In addition, an opening/closing mechanism (not illustrated) for opening and closing the jaw 6 with respect to the portion of the distal end side A1 of the ultrasound probe 8 according to the operation of the operation knob 41 by the operator is provided inside the handle 4 and the sheath 5 described above.

In the jaw 6, a resin pad 61 (see FIG. 5) is attached to a surface facing the ultrasound probe 8. The pad 61 has insulation, and therefore has a function of preventing the jaw 6 and the ultrasound probe 8 from being short-circuited. Further, the pad 61 has a function of preventing the ultrasound probe 8, which is performing ultrasound vibration, from being damaged due to a collision with the jaw 6 when the incision of the target site by the ultrasound vibration is completed.

Figure 2:
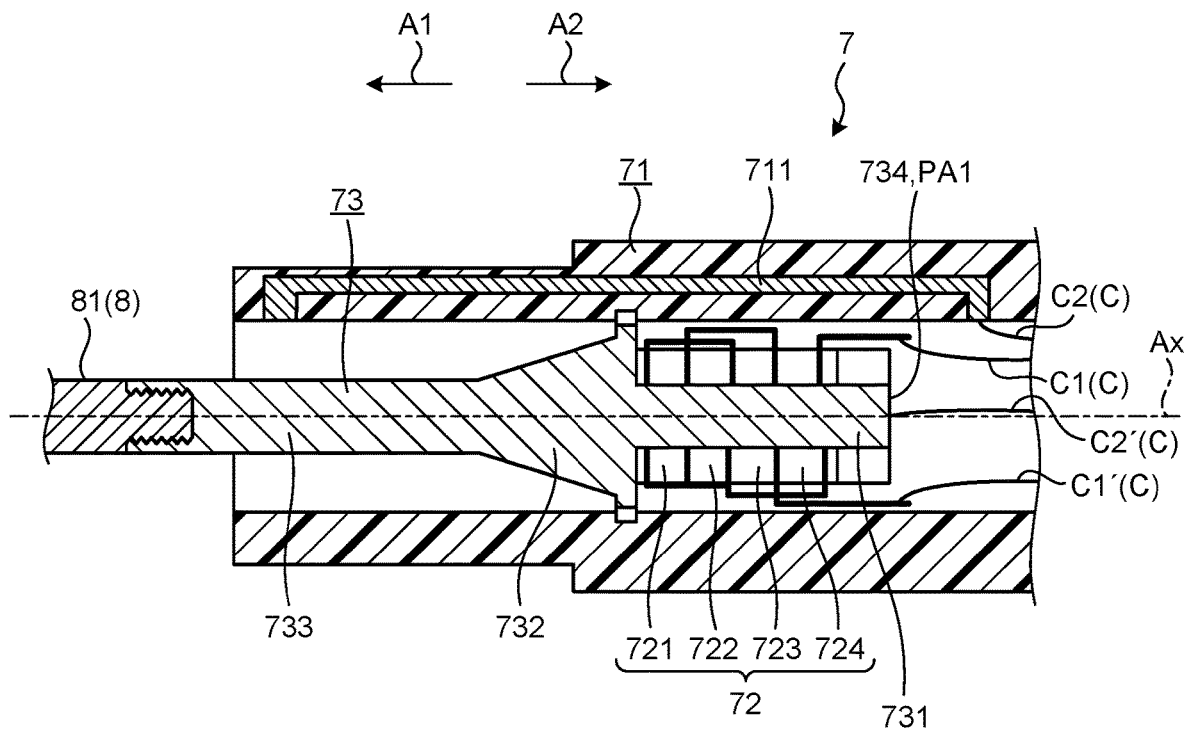
FIG. 2 is a cross-sectional view illustrating a transducer unit.

FIG. 2 is a cross-sectional view illustrating the transducer unit 7. Specifically, FIG. 2 is a cross-sectional view of the transducer unit 7 cut on a plane including the central axis Ax.

As illustrated in FIG. 2, the transducer unit 7 includes a transducer case 71, an ultrasound transducer 72, and a horn 73.

The transducer case 71 extends linearly along the central axis Ax and is attached to the handle 4 by inserting a part of the distal end side A1 from the proximal end side A2 of the handle 4 into the inside of the handle 4. In the state in which the transducer case 71 is attached to the handle 4, the end portion of the distal end side A1 is connected to the end portion of the proximal end side A2 of the sheath 5.

The ultrasound transducer 72 is housed inside the transducer case 71 and generates ultrasound vibration under the control of the control device 3. In this exemplary embodiment, the ultrasound vibration is a longitudinal vibration that vibrates in the direction along the central axis Ax. As illustrated in FIG. 2, this ultrasound transducer 72 is a BLT that includes a plurality of piezoelectric elements 721 to 724 stacked along the central axis Ax. Although four piezoelectric elements 721 to 724 are provided in this exemplary embodiment, the number of piezoelectric elements is not limited to four and may be any other number.

The horn 73 is housed inside the transducer case 71, and expands the amplitude of the ultrasound vibration generated by the ultrasound transducer 72. The horn 73 has a long shape that linearly extends along the central axis Ax. Then, as illustrated in FIG. 2, the horn 73 includes a transducer mounting portion 731 in which the ultrasound transducer 72 is mounted from the proximal end side A2 to the distal end side A1, a cross-sectional area changing portion 732 that has a shape in which a cross-sectional area decreases toward the distal end side A1 and increases the amplitude of the ultrasound vibration, and a probe mounting portion 733 in which the ultrasound probe 8 is mounted.

The ultrasound probe 8 has a long shape that linearly extends along the central axis Ax, and as illustrated in FIG. 1, is inserted into the sheath 5 while the portion of the distal end side A1 portion protrudes outward. Further, the end portion of the proximal end side A2 of the ultrasound probe 8 is connected to the probe mounting portion 733 as illustrated in FIG. 2. Then, the ultrasound probe 8 transmits the ultrasound vibration generated by the ultrasound transducer 72 from the end portion of the proximal end side A2 to the end portion of the distal end side A1 via the horn 73, and treats the target site by applying the ultrasound vibration from the end portion of the distal end side A1 to the target site. Note that a detailed configuration of the ultrasound probe 8 will be described below.

The control device 3 is electrically connected to the ultrasound treatment tool 2 by an electric cable C (FIG. 1), and integrally controls the operation of the ultrasound treatment tool 2. As illustrated in FIG. 1, the control device 3 includes an ultrasound current supply unit 31, a high frequency current supply unit 32, and an energy control unit 33.

Here, as illustrated in FIG. 2, the ultrasound transducer 72 is joined to a pair of transducer lead wires C1 and C1' constituting the electric cable C.

Then, under the control of the energy control unit 33, the ultrasound current supply unit 31 supplies AC power to the ultrasound transducer 72 via the pair of transducer lead wires C1 and C1'. Thereby, the ultrasound transducer 72 generates ultrasound vibration.

Here, as illustrated in FIG. 2, the transducer case 71 is provided with a first conductive portion 711 extending from the end portion of the proximal end side A2 to the end portion of the distal end side A1. Further, although not specifically illustrated, the sheath 5 is provided with a second conductive portion that extends from the end portion of the proximal end side A2 to the end portion of the distal end side A1 and electrically connects between the first conductive portion 711 and the jaw 6. Further, a high frequency lead wire C2 constituting the electric cable C is joined to the end portion of the proximal end side A2 of the first conductive portion 711. Further, a high frequency lead wire C2' that constitutes the electric cable C is joined to the transducer mounting portion 731.

Then, the high frequency current supply unit 32 supplies a high frequency current between the jaw 6 and the ultrasound probe 8 via the pair of high frequency lead wires C2 and C2', the first conductive portion 711, the second conductive portion, and the horn 73 under the control of the energy control unit 33. As a result, a high frequency current flows in a target site held between the jaw 6 and the portion of the distal end side A1 of the ultrasound probe 8. That is, the jaw 6 and the ultrasound probe 8 also function as a high frequency electrode. In other words, the ultrasound treatment tool 2 also functions as a bipolar treatment tool because the jaw 6 and the ultrasound probe 8 function as a pair of high frequency electrodes.

The energy control unit 33 is, for example, a central processing unit (CPU), a field-programmable gate array (FPGA), or the like, and when an operation button 42 is pressed by an operator, the energy control unit 33 controls the operations of the ultrasound current supply unit 31 and the high frequency current supply unit 32 according to a predetermined control program.

Configuration of Ultrasound Probe

Next, a detailed configuration of the above-described ultrasound probe 8 will be described.

Figure 3:
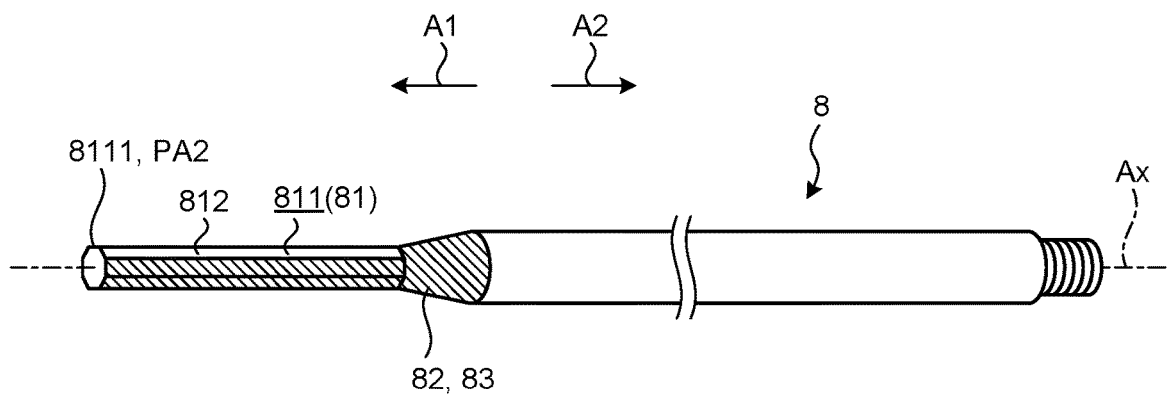
FIG. 3 is a perspective view illustrating an ultrasound probe.
Figure 4:
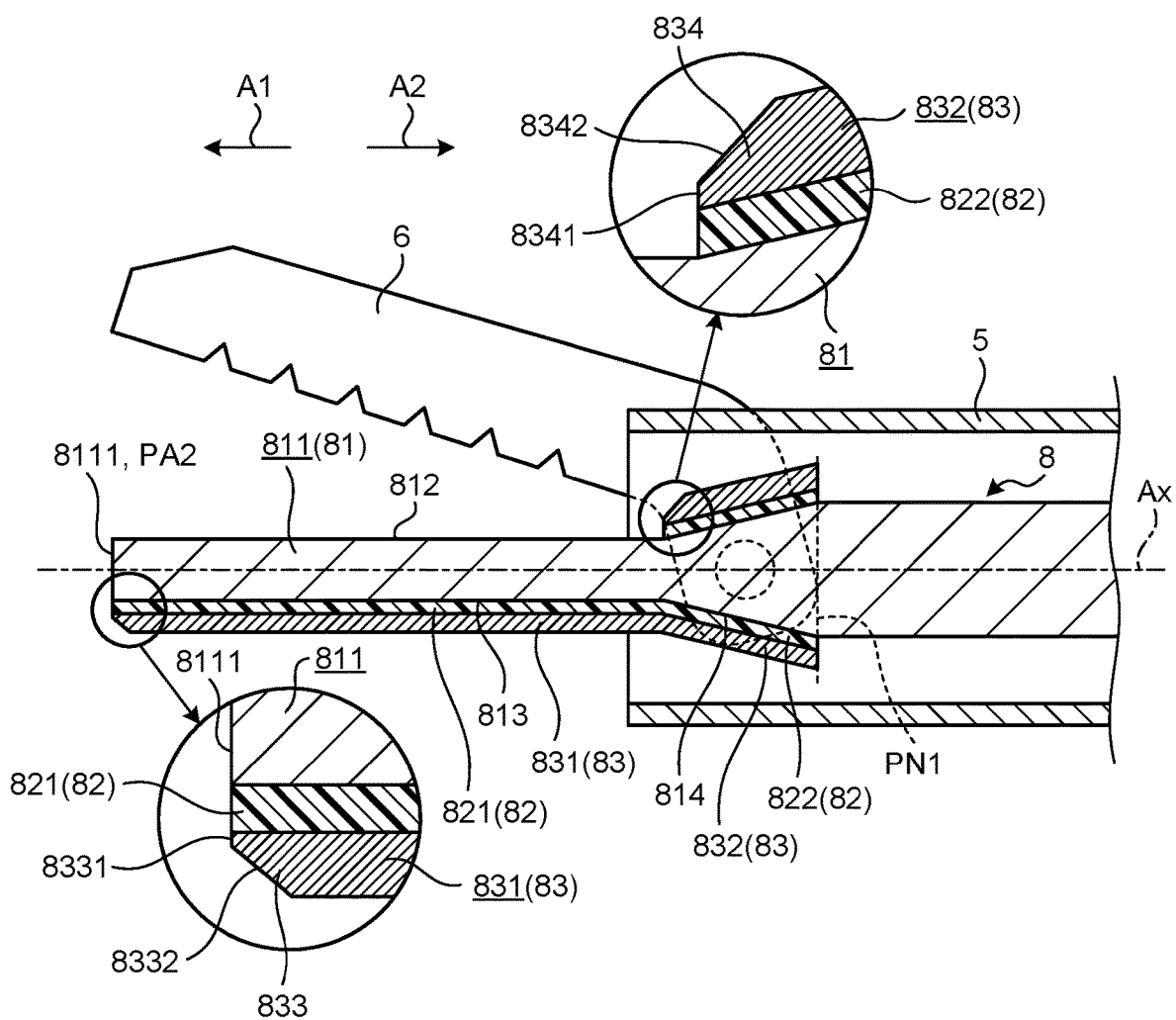
FIG. 4 is a cross-sectional view illustrating a distal end portion of the ultrasound probe.
Figure 5:
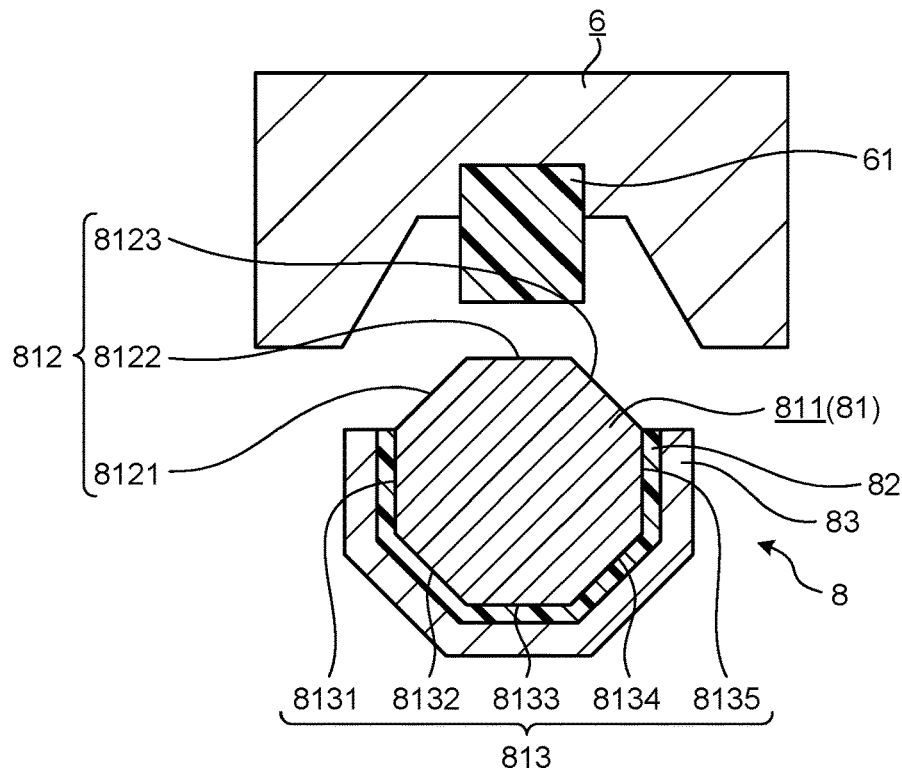
FIG. 5 is a cross-sectional view illustrating the distal end portion of the ultrasound probe.

FIG. 3 is a perspective view illustrating the ultrasound probe 8. FIGS. 4 and 5 are cross-sectional views illustrating the distal end portion of the ultrasound probe 8. Specifically, FIG. 4 is a cross-sectional view of the ultrasound probe 8 cut on a plane including the central axis Ax and passing through a treatment surface 812. FIG. 5 is a cross-sectional view of the ultrasound probe 8 cut on a plane orthogonal to the central axis Ax and passing through a treatment portion 811.

The ultrasound probe 8 includes a probe body 81, a coating portion 82, and a mold portion 83, as illustrated in FIGS. 3 to 5. Note that in FIG. 3, for convenience of description, positions where the coating portion 82 and the mold portion 83 are provided are shaded.

The probe body 81 is made of, for example, a titanium alloy or the like, and has a long shape that linearly extends along the central axis Ax as illustrated in FIG. 3. Then, the probe body 81 transmits the ultrasound vibration generated by the ultrasound transducer 72 from the end portion of the proximal end side A2 to the end portion of the distal end side A1 via the horn 73.

Here, the probe body 81 performs the longitudinal vibration by transmitting ultrasound vibration from the end portion of the proximal end side A2 to the end portion of the distal end side A1. Then, the probe body 81, the horn 73, and the ultrasound transducer 72 become one vibrating body that performs the longitudinal vibration by the ultrasound vibration at a predetermined resonance frequency generated by the ultrasound transducer 72. For this reason, a proximal end surface 734 (FIG. 2) of the horn 73 is located at the most proximal end antinode position PA1 (FIG. 2) located on the most proximal end side A2 among positions of antinodes of the longitudinal vibration. Further, a distal end surface 8111 (FIGS. 3 and 4) of the probe body 81 is located at the most distal end antinode position PA2 (FIGS. 3 and 4) located on the most distal end side A1 among the positions of the antinodes of the longitudinal vibration. Note that the longitudinal vibration has a frequency of, for example, 47 kHz, and an amplitude of, for example, 80 µm at the most distal end antinode position PA2.

In the probe body 81, the end portion of the distal end side A1 functions as a treatment portion 811 according to the disclosure for treating the target site while holding the target site between the end portion of the distal end side A1 and the jaw 6. The treatment portion 811 is a portion located on the distal end side A1 rather than the most distal end node position PN1 (FIG. 4) located on the most distal end side A1 among positions of nodes of longitudinal vibration. The treatment portion 811 is positioned while protruding from the sheath 5 to the distal end side A1.

In the exemplary embodiment illustrated in FIG. 5, the treatment portion 811 has an octagonal cross section shape, in which three sides 8121 to 8123 of the octagonal cross section shape are positioned so as to face the jaw 6. Then, surfaces corresponding to the three sides 8121 to 8123 function as a treatment surface 812 that contacts the target site and treats the target site while holding the target site between the treatment portion 811 and the jaw 6.

Here, the distal end surface 8111 constituting the treatment portion 811 is not parallel to the central axis Ax. That is, the distal end surface 8111 is not parallel to a vibration direction of the longitudinal vibration. When such a distal end surface 8111 vibrates longitudinally, pressurization and depressurization are periodically repeated in the vicinity of the distal end surface 8111. Particularly, since the distal end surface 8111 is located at the most distal end antinode position PA2, the amplitude is large. That is, the pressurizing/depressurizing action becomes large in the vicinity of the distal end surface 8111. Then, when the distal end surface 8111 is located in a liquid, or when the distal end surface 8111 is longitudinally vibrated in the state where the liquid is present in the vicinity of the distal end surface 8111, in the vicinity of the distal end surface 8111, bubbles (cavities) are generated in the liquid due to the pressurizing and depressurizing action. The generated bubbles disappear due to a force acting in the depressurization in the vicinity of the distal end surface 8111. Then, as the bubbles disappear, a large impact energy is generated. Note that the phenomenon described above is called a cavitation phenomenon.

The coating portion 82 is a portion that covers the surface of the probe body 81, and is made of a material that has electrical insulation and has a lower thermal conductivity than the probe body 81. In an exemplary embodiment, the coating portion 82 contains polyether ether ketone (PEEK) as a main component, and is made of a material containing a linear expansion adjusting filler having a smaller coefficient of linear expansion than that of the main component. Note that as the linear expansion adjusting filler, for example, mica can be used. In addition, the linear expansion adjusting filler is preferably contained in an amount of 0.1% by mass or more and 50% by mass or less.

Here, the region in which the coating portion 82 is provided is as follows.

The coating portion 82 covers a part of the surface of the treatment portion 811. Specifically, the coating portion 82 is provided in a region excluding the distal end surface 8111 and the treatment surface 812 in the treatment portion 811. That is, the coating portion 82 is provided on a surface 813 (FIGS. 4 and 5) corresponding to five sides 8131 to 8135 (FIG. 5) excluding the treatment surface 812 in the treatment portion 811 having an octagonal cross section shape. In the following, in the coating portion 82, the portion provided on the surface 813 is referred to as a first coating portion 821 (FIG. 4). In addition, the coating portion 82 includes a second coating portion 822 (FIG. 4) that is continuously provided on the proximal end side A2 with respect to the first coating portion 821. The second coating portion 822 extends over the entire circumference in a circumferential direction around the central axis Ax on a surface 814 (FIG. 4) continuous to the proximal end side A2 with respect to the treatment portion 811. In addition, the second coating portion 822 is positioned at a position close to the most distal end node position PN1. In other words, the second coating portion 822 is positioned at a position other than the antinode position of the longitudinal vibration. Further, the second coating portion 822 is positioned inside the sheath 5.

Note that the coating portion 82 is formed, for example, as illustrated below.

A liquid containing a scale-like linear expansion adjusting filler (mica) in a granular main component (PEEK) is sprayed onto the surface of the probe body 81. Then, the coating portion 82 is formed by heating the liquid.

Although not specifically illustrated, the surfaces 813 and 814 of the probe body 81 covered with the coating portion 82 are subjected to surface treatment in order to improve the adhesion strength with the coating portion 82. Examples of the surface treatment can include surface treatment that increases the surface roughness by sandblasting. Then, the coating portion 82 is formed on the surfaces 813 and 814 that are subjected to the surface treatment. That is, by removing the oxide film from the surfaces 813 and 814 by the surface treatment and applying an anchor effect between the surfaces 813 and 814 and the coating portion 82, and a stress effect from an uneven surface, the adhesion strength of the surfaces 813 and 814 with the coating portion 82 is improved.

The mold portion 83 is integrally formed on the coating portion 82 by, for example, insert molding or outsert molding, using a material that has electrical insulation and has a lower thermal conductivity than the probe body 81. In an exemplary embodiment, the mold portion 83 is made of a material that contains the PEEK as a main component and a glass filler with respect to the main component. Note that the glass filler is preferably contained in an amount of 10% by mass or more and 40% by mass or less. Here, the region in which the mold portion 83 is provided is the same as the region in which the coating portion 82 is provided. That is, as illustrated in FIG. 4, the mold portion 83 includes a first mold portion 831 provided on the whole of the first coating portion 821 and a second mold portion 832 provided on the whole of the second coating portion 822. The second mold portion 832 corresponds to an annular portion according to the disclosure. Further, since the second mold portion 832 is provided on the whole of the second coating portion 822, the second mold portion 832 is positioned at a position close to the most distal end node position PN1. In other words, the second mold portion 832 is positioned at a position other than the antinode position of the longitudinal vibration. Further, the second mold portion 832 is positioned inside the sheath 5. As a result, even if the mold portion 83 in the vicinity of the antinode position of the longitudinal vibration peels off due to abnormal heat or stress from the outside, the presence of the second coating portion 822 and the second mold portion 83 can prevent the mold portion 83 from falling off.

The mold portion 83 is provided on the whole of the coating portion 82, but can be provided on a part of the coating portion 82 without being limited thereto. Further, the second mold portion 832 is positioned at a position other than the antinode position of the longitudinal vibration, but the disclosure is not limited thereto, and a part of the second mold portion 832 may be positioned at the antinode position of the longitudinal vibration.

Note that the mold portion 83 is formed, for example, as illustrated below.

The probe body 81 having a coating portion 82 formed thereon is provided in the die. Next, the temperature of the die is set to be a predetermined temperature. Here, the predetermined temperature may be, for example, a glass transition point or higher or a melting point or lower of the material forming the mold portion 83. Next, the material forming the molten mold portion 83 is injected into the die to mold the mold portion 83. Here, the mold portion 83 and the coating portion 82 have the same main component. Therefore, by molding the mold portion 83 by the method described above, the mold portion 83 and the coating portion 82 are joined to each other by fusing the main components. When injecting the material forming the molten mold portion 83 into the die, in order to prevent the temperature of the molten material from being lowered due to the die, the injection pressure or the injection speed at the time of injection are preferably set to be higher than the general injection pressure or the injection speed.

The mold portion 83 described above has a predetermined thickness dimension in regions other than the first and second end portions 833 and 834 (FIG. 4) illustrated below. Here, by securing a thickness dimension of 0.1 mm or more as the predetermined thickness dimension, it is possible to secure better heat insulation than the configuration in which only the coating portion 82 is provided. Further, in order to ensure moldability, it is more preferable to secure a thickness dimension of 0.2 mm or more as the predetermined thickness dimension. Further, by setting the thickness dimension to 2.0 mm or less as the predetermined thickness dimension, it is possible to prevent the size of the apparatus from increasing and to ensure the insertability into a trocar or the like. Further, if the predetermined thickness dimension becomes too large, the mass increases, and furthermore, a difference in followability to vibration between the probe body 81 made of metal and the mold portion 83 made of resin occurs, which can cause cracks and peeling. In addition, the predetermined thickness dimension is increased, and thus the resonance frequency is affected, and furthermore, the impedance is increased, and thus a vibration loss (vibration damping) occurs and the heat energy is generated accordingly, so heat generation is likely to increase. From the above, it is preferable that the predetermined thickness dimension is, for example, 0.1 mm or more and 2.0 mm or less. Further, the predetermined thickness dimension is more preferably 0.2 mm or more and 1.0 mm or less. Furthermore, the thickness dimension of the mold portion 83 is larger than the thickness dimension of the coating portion 82.

The first end portion 833 corresponds to the end portion according to the disclosure. As illustrated in FIG. 4, the first end portion 833 is located at the end portion of the distal end side A1 of the first mold portion 831. This first end portion 833 includes an end surface 8331 angled to the central axis Ax. In an exemplary embodiment, the end surface 8331 is substantially orthogonal to the central axis Ax. In addition, the first end portion 833 has a first inclined surface 8332 that reduces the thickness dimension of the first end portion 833 toward the end surface 8331. The thickness dimension of the first end portion 833 on the end surface 8331 is smaller than the above-described predetermined thickness dimension. In other words, the thickness dimension of the first end portion 833 on the end surface 8331 is smaller than a thickness dimension of other regions in the mold portion 83.

The second end portion 834 corresponds to the end portion according to the disclosure. As illustrated in FIG. 4, the second end portion 834 is an end portion of the distal end side A1 of the second mold portion 832 and is located at a portion facing the treatment surface 812 side. This second end portion 834 includes an end surface 8341 angled to the central axis Ax. In an exemplary embodiment, the end surface 8331 is substantially orthogonal to the central axis Ax. In addition, the second end portion 834 has a second inclined surface 8342 that reduces the thickness dimension of the second end portion 834 toward the end surface 8341. Note that the thickness dimension of the second end portion 834 on the end surface 8341 is substantially the same as the thickness dimension of the first end portion 833 on the end surface 8331 described above.

The reason why the PEEK is used as the main component of the coating portion 82 and the mold portion 83 described above is as follows.

In the ultrasound probe 8, the temperature rises to about 300° C. due to frictional heat. That is, the coating portion 82 and the mold portion 83 provided on the ultrasound probe 8 need to withstand the temperature. In addition, the coating portion 82 and the mold portion 83 are a portion that is inserted into a body and comes into contact with a biological tissue, and therefore require biocompatibility. As an example of a material satisfying these requirements, the PEEK may be used as the main component of the coating portion 82 and the mold portion 83.

Operation of Treatment Apparatus

Next, the operation of the treatment apparatus 1 described above will be described.

An operator holds the ultrasound treatment tool 2 by hand, and inserts the distal end portion of the ultrasound treatment tool 2 into an abdominal cavity through the abdominal wall using, for example, the trocar or the like. Then, the operator operates an operation knob 41 to open and close the jaw 6 with respect to the treatment portion 811, thereby holding a target site by the jaw 6 and the treatment portion 811. After this, the operator presses the operation button 42. Then, the energy control unit 33 executes the following control.

The energy control unit 33 controls the operation of the high frequency current supply unit 32, and supplies the high frequency current between the jaw 6 and the ultrasound probe 8 via the pair of high frequency lead wires C2 and C2', the first conductive portion 711, the second conductive portion, and the horn 73. Further, the energy control unit 33 controls the operation of the ultrasound current supply unit 31 at substantially the same time as the supply of the high frequency current between the jaw 6 and the ultrasound probe 8, and supplies AC power to the ultrasound transducer 72 via the pair of transducer lead wires C1 and C1', thereby generating the ultrasound vibration in the ultrasound transducer 72. That is, Joule heat is generated at the target site due to the flowing of the high frequency current. Further, the longitudinal vibration of the treatment portion 811 generates the frictional heat between the treatment surface 812 and the target site. Then, the target site is incised while coagulating.

According to the exemplary embodiment described above, the following effects are obtained.

In the ultrasound probe 8 according to this embodiment, the probe body 81 has a back surface that is opposite to the treatment surface 812 in the treatment portion 811 and is covered with the coating portion 82, and has the mold portion 83 that is integrally formed on the coating portion 82. That is, the back surface is covered with the coating portion 82 and the mold portion 83 that have a lower thermal conductivity than the probe body 81.

Therefore, even when the back surface opposite to the treatment surface 812 in the ultrasound probe 8 comes into contact with a site other than the target site in the biological tissue, the temperature of the back surface is suppressed from rising by the coating portion 82 and the mold portion 83, so the unintended action is not exerted on the biological tissue. In particular, since not only the coating portion 82 but also the mold portion 83 is provided, the thickness dimension of the portion having the lower thermal conductivity than the probe body 81 can increase. Therefore, as compared with the configuration in which only the coating portion 82 is provided, the temperature of the back surface can be further suppressed from rising.

In addition, the coating portion 82 and the mold portion 83 are integrally formed with the probe body 81. That is, there is no gap between the probe body 81 and the coating portion 82 and the mold portion 83. Therefore, when the treatment is performed by the ultrasound treatment tool 2, it is possible to prevent the biological tissue from entering the gap and the biological tissue from clogging with the gap.

From the above, according to the ultrasound probe 8 according to this embodiment, it is possible to prevent the biological tissue from clogging while avoiding exerting the unintended action on the biological tissue.

Further, in the ultrasound probe 8 according to this embodiment, the coating portion 82 and the mold portion 83 are made of a material having electrical insulation. Therefore, the high frequency current concentratedly flows in the portion where the coating portion 82 and the mold portion 83 are not provided. On the other hand, since the coating portion 82 and the mold portion 83 are not provided in the range in contact with the target site, the high frequency current efficiently flows in the target site. In other words, it is possible to reduce the flow of the high frequency current in the biological tissue or the like other than the target site located on the back surface opposite to the treatment surface 812 in the treatment portion 811. As a result, it is possible to realize the treatment performance, shorten the high frequency treatment time, reduce the unnecessary invasion of the high frequency current into surrounding tissues, and the like.

Further, in the ultrasound probe 8 according to this embodiment, the coating portion 82 and the mold portion 83 each have a common main component (PEEK), and are joined to each other by fusing the main components. Therefore, the adhesion of the mold portion 83 to the coating portion 82 can be improved.

In addition, in the ultrasound probe 8 according to this embodiment, the mold portion 83 is made of a material containing a glass filler with respect to the PEEK. Therefore, the heat resistant temperature of the mold portion 83 can be improved and the deformation of the mold portion 83 due to heat can be suppressed.

Further, in the ultrasound probe 8 according to this embodiment, the coating portion 82 is made of a material containing a linear expansion adjusting filler (mica) having a smaller coefficient of linear expansion than the PEEK. Therefore, the difference in coefficient of linear expansion between the probe body 81 and the coating portion 82 can be reduced, and the adhesion of the coating portion 82 to the probe body 81 can be improved.

However, comparing metals such as a titanium alloy with resins such as PEEK, the resin has a larger coefficient of linear expansion. In the ultrasound probe 8, the temperature rises to about 300° C. due to frictional heat. Therefore, in the case where the metal is simply covered with the resin, a large stress is generated between the metal and the resin due to the difference in coefficient of linear expansion. In order to prevent damage due to the stress, in this embodiment, the coating portion 82 is provided between the probe body 81 and the mold portion 83. The coating portion 82 is made of a material containing mica having a smaller coefficient of linear expansion than resin. Therefore, the coefficient of linear expansion of the coating portion 82 is larger than that of the probe body 81 and smaller than that of the mold portion 83. More ideally, the coefficient of linear expansion of the coating portion 82 is preferably a coefficient of linear expansion near the middle of the coefficient of linear expansion of the probe body 81 and the mold portion 83. That is, the relationship of the coefficient of linear expansion is preferably the relationship of probe body 81>coating portion 82>mold portion 83. With such a configuration, it is possible to provide the mold portion 83 having sufficient adhesion even in the ultrasound probe 8 which is exposed to high temperature by the frictional heat.

In addition, in the ultrasound probe 8 according to this embodiment, the mold portion 83 includes the first and second end portions 833 and 834 having the end surfaces 8331 and 8341 angled to the central axis Ax. These first and second end portions 833 and 834 have a shape in which the thickness dimension decreases toward the end surfaces 8331 and 8341. Further, the thickness dimensions of the first and second end portions 833 and 834 on the end surfaces 8331 and 8341 are smaller than the thickness dimensions of other regions in the mold portion 83. Therefore, by reducing the area of the end surfaces 8331 and 8341, the occurrence of the above-described cavitation phenomenon on the end surfaces 8331 and 8341 can be suppressed. Further, when considering the fluidity of the material forming the molten mold portion 83 in the die, it is necessary to secure a predetermined thickness dimension as the end surfaces 8331 and 8341. That is, by keeping the end surfaces 8331 and 8341 with the minimum required thickness dimension without being lost, the moldability of the mold portion 83 can be improved while suppressing the occurrence of the cavitation phenomenon.

In addition, in the ultrasound probe 8 according to this embodiment, the mold portion 83 includes the second mold portion 832 extending over the entire circumference in the circumferential direction around the central axis Ax. Therefore, as compared with the configuration in which only the first mold portion 831 is provided, it is possible to prevent the mold portion 83 from falling off from the probe body 81.

In particular, the second mold portion 832 is provided at a position other than the antinode position of the longitudinal vibration. Therefore, it is possible to suppress the influence of the frictional heat generated between the probe body 81 and the second mold portion 832 according to the longitudinal vibration of the probe body 81, and effectively prevent the mold portion 83 from falling off from the probe body 81.

Further, the second mold portion 832 is positioned inside the sheath 5. Therefore, the second mold portion 832 can be protected by the sheath 5, and the mold portion 83 can be effectively prevented from falling off from the probe body 81.

As described above, the coating portion 82 and the mold portion 83 that are firmly joined to the probe body 81 become a resonator together with the probe body 81. As a result, it is possible to improve the desired performance by minimizing the adverse effect on the visibility and operability while minimizing the vibration load.

Figure 6:
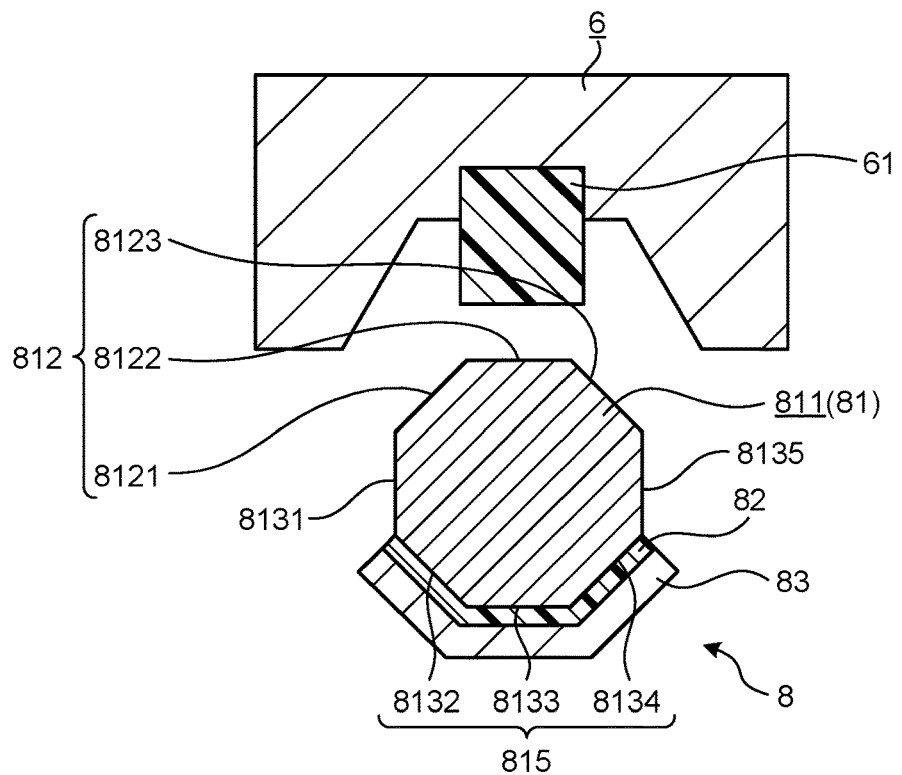
FIG. 6 is a diagram illustrating a distal end portion of the ultrasound probe according to an exemplary embodiment.
Figure 7:
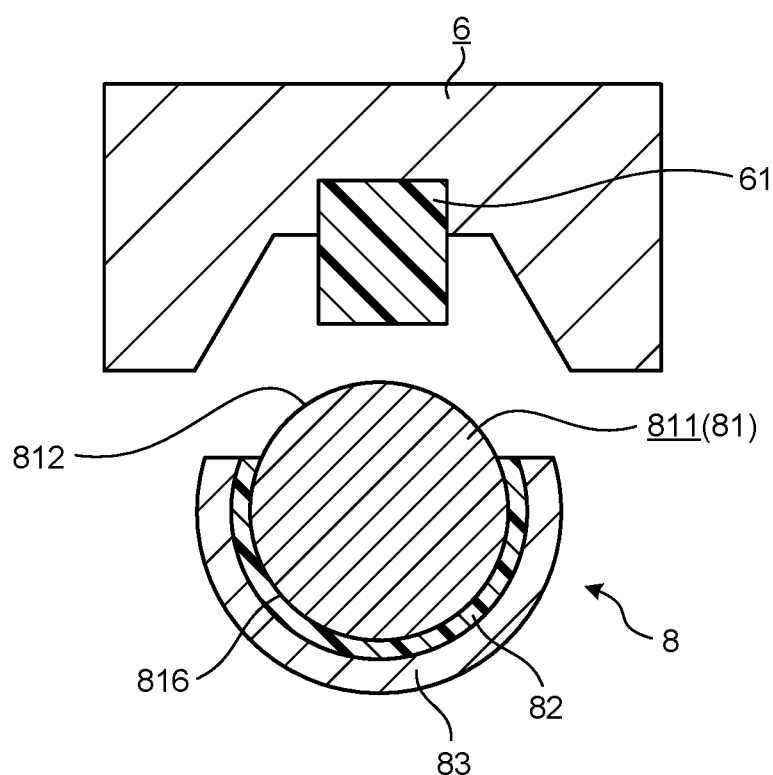
FIG. 7 is a diagram illustrating a distal end portion of the ultrasound probe according to an exemplary embodiment.

FIG. 6 is a diagram illustrating an exemplary modification of the above embodiment. FIG. 7 is a diagram illustrating another exemplary modification of the above embodiment. Specifically, FIGS. 6 and 7 are cross-sectional views corresponding to FIG. 5.

In the exemplary embodiment described above, the coating portion 82 and the mold portion 83 are provided on a surface 813 corresponding to five sides 8131 to 8135 excluding the treatment surface 812 in the treatment portion 811 having an octagonal cross section shape, but the disclosure is not limited thereto. For example, as in the exemplary modification illustrated in FIG. 6, in the treatment portion 811 having the octagonal cross section shape, the coating portion 82 and the mold portion 83 may be provided on a surface 815 corresponding to the three sides 8132 to 8134 separated from the treatment surface 812 among the five sides 8131 to 8135 excluding the treatment surface 812.

Further, in the exemplary embodiment described above, the shape of the treatment portion 811 is not limited to the shape described in the embodiment described above, and the treatment portion 811 may have other shape. For example, as in the exemplary modification illustrated in FIG. 7, the treatment portion 811 may have a substantially circular cross section shape. At this time, on the outer circumference surface of the treatment portion 811, the portion facing the jaw 6 functions as the treatment surface 812. The coating portion 82 and the mold portion 83 are provided on an outer circumference surface 816 other than the treatment surface 812 on the outer circumference surface of the treatment portion 811.

Next, another exemplary embodiment will be described.
In the following description, the same reference numerals are given to the same components as those of the exemplary embodiment described above, and a detailed description thereof will be omitted or simplified.

Figure 8:
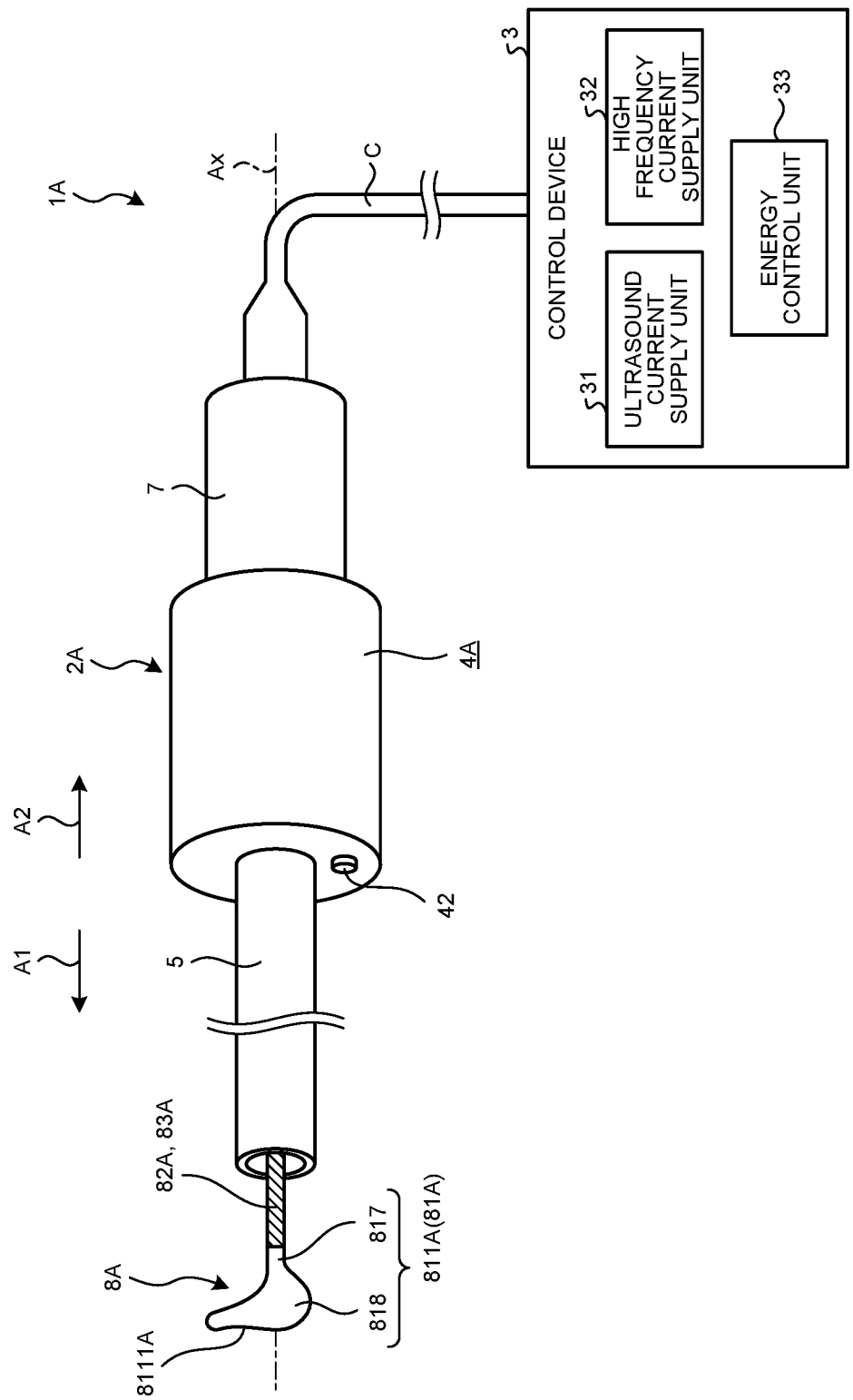
FIG. 8 is a diagram illustrating a treatment apparatus according to an exemplary embodiment.
Figure 9:
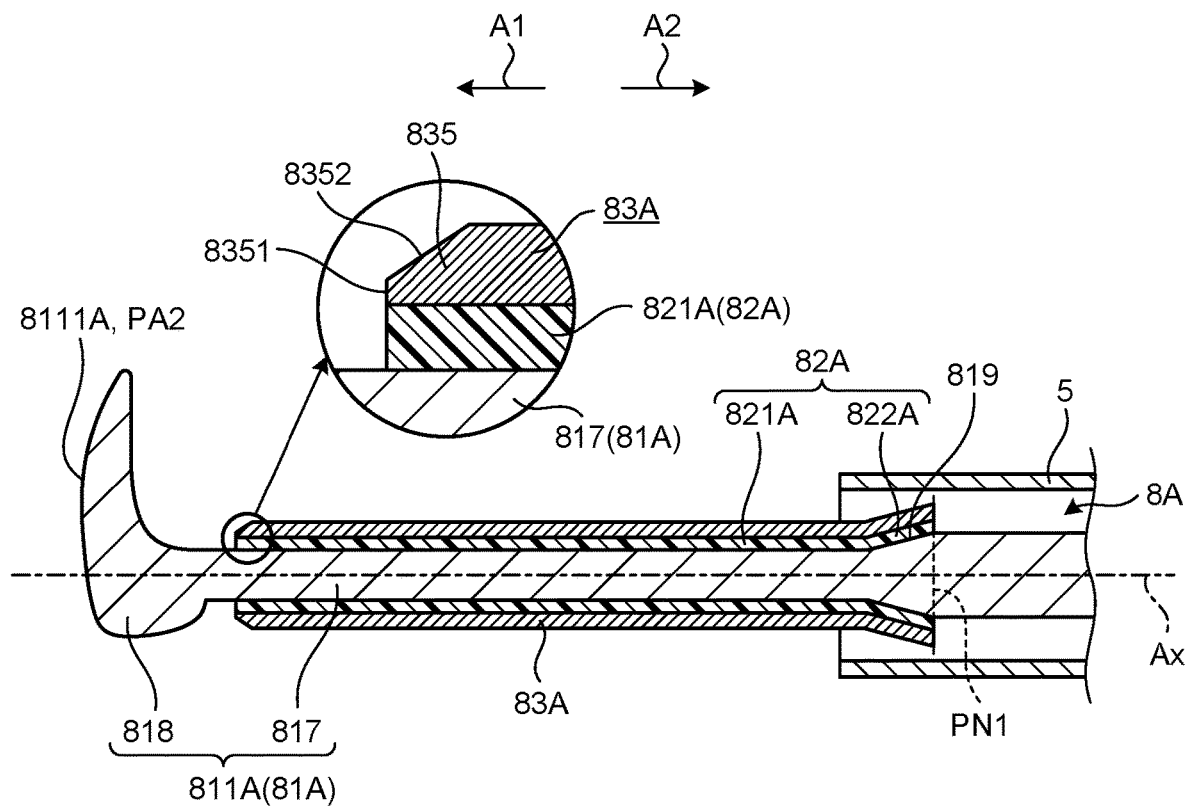
FIG. 9 is a cross-sectional view illustrating the distal end portion of the ultrasound probe.
Figure 10:
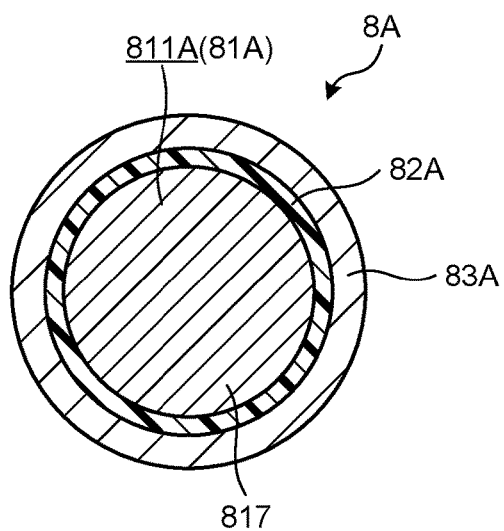
FIG. 10 is a cross-sectional view illustrating the distal end portion of the ultrasound probe.

FIG. 8 is a diagram illustrating a treatment apparatus 1A according to another exemplary embodiment. FIGS. 9 and 10 are cross-sectional views illustrating a distal end portion of an ultrasound probe 8A. Specifically, FIG. 9 is a cross-sectional view of the ultrasound probe 8A cut on a plane including the central axis Ax. FIG. 10 is a cross-sectional view of the ultrasound probe 8A cut on a plane orthogonal to the central axis Ax and passing through a column portion 817.

As illustrated in FIGS. 8 to 10, the treatment apparatus 1A according to this embodiment employs an ultrasound treatment tool 2A different from the ultrasound treatment tool 2, compared with the treatment apparatus 1 described in the exemplary embodiment described above. The ultrasound treatment tool 2A employs a handle 4A and an ultrasound probe 8A different from the handle 4 and the ultrasound probe 8, and does not have the jaw 6.

As illustrated in FIG. 8, the handle 4A has a different shape from the handle 4 described in the exemplary embodiment described above. Further, the handle 4A is not provided with an operation knob 41.

As illustrated in FIGS. 8 to 10, the ultrasound probe 8A employs a probe body 81A having a treatment portion 811A having a shape different from that of the treatment portion 811, compared with the probe body 81 described in the embodiment described above.

As illustrated in FIG. 8 or FIG. 9, the treatment portion 811A includes a column portion 817 that linearly extends along the central axis Ax and a hook-shaped distal end portion 818 that is provided at an end portion of a distal end side A1 of the column portion 817 and extends in a direction substantially orthogonal to the central axis Ax.

The shape of the distal end portion 818 is not limited to the hook shape, but the distal end portion 818 may have other shapes such as a spatula shape.

As illustrated in FIG. 9, the treatment portion 811A is located on the distal end side A1 rather than the most distal end node position PN1 located on the most distal end side A1 among nodes of a longitudinal vibration, as in the embodiment described above. Further, a distal end surface 8111A in the treatment portion 811A is located at the most distal end antinode position PA2 located on the most distal end side A1 among the antinode positions of the longitudinal vibration. In addition, the treatment portion 811A is positioned while protruding from the sheath 5 to the distal end side A1.

Further, as illustrated in FIGS. 8 to 10, the ultrasound probe 8A is different from the ultrasound probe 8 described in the embodiment described above in terms of a region in which a coating portion 82A and a mold portion 83A are provided. Note that in FIG. 8, for convenience of description, positions where the coating portion 82A and the mold portion 83A are provided are shaded. In addition, a material and a forming method of the coating portion 82A and the mold portion 83A are the same as those of the coating portion 82 and mold portion 83 described in the embodiment described above.

The coating portion 82A covers a part of the surface of the treatment portion 811A. Specifically, the coating portion 82A is formed on the entire circumference of an outer circumference surface of a column portion 817, except for the distal end portion 818 in the treatment portion 811A. In the following, in the coating portion 82A, the portion provided on the entire circumference of the outer circumference surface of the column portion 817 is referred to as a first coating portion 821A (FIG. 9). In addition, the coating portion 82A includes a second coating portion 822A (FIG. 9)

that is continuously provided on a proximal end side A2 with respect to the first coating portion 821A. The second coating portion 822A extends over the entire circumference in a circumferential direction around the central axis Ax on a surface 819 continuous to the proximal end side A2 with respect to the surface of the treatment portion 811A. In addition, the second coating portion 822A is positioned at a position close to the most distal end node position PN1. In other words, the second coating portion 822A is positioned at a position other than the antinode position of the longitudinal vibration. Further, the second coating portion 822A is positioned inside the sheath 5.

The mold portion 83A is integrally formed on the entire coating portion 82A. The mold portion 83A is not provided over the whole of the coating portion 82A, but may be provided on a part of the coating portion 82A.

The mold portion 83A has a predetermined thickness dimension in the region other than an end portion 835 (FIG. 9) illustrated below. Here, it is preferable that the predetermined thickness dimension is, for example, 0.1 mm or more and 2.0 mm or less. In addition, the thickness dimension of the mold portion 83A is larger than that of the coating portion 82A.

The end portion 835 is located at the end portion of the distal end side A1 of the mold portion 83A. The end portion 835 includes an end surface 8351 angled to the central axis Ax. In this embodiment, the end surface 8351 is orthogonal to the central axis Ax. In addition, the end portion 835 has an inclined surface 8352 that reduces the thickness dimension of the end portion 835 toward the end surface 8351. Note that the thickness dimension of the end portion 835 on the end surface 8351 is smaller than the above-described predetermined thickness dimension.

Then, the treatment apparatus 1A according to the exemplary embodiment shown in FIGS. 8-10 operates as described below.

An operator holds the ultrasound treatment tool 2A by hand and brings the distal end portion 818 into contact with the target site. After this, the operator presses the operation button 42. Then, the energy control unit 33 executes the following control.

An energy control unit 33 controls an operation of a high frequency current supply unit 32, and supplies a high frequency current between the ultrasound probe 8A and a counter plate (not illustrated) attached to a surface of a subject. Further, the energy control unit 33 controls the operation of the ultrasound current supply unit 31 at substantially the same time as the supply of the high frequency current between the ultrasound probe 8A and the counter plate, and supplies the AC power to the ultrasound transducer 72 to generate ultrasound vibration on the ultrasound transducer 72. That is, Joule heat is generated at the target site due to the flowing of the high frequency current. Further, the longitudinal vibration of the treatment portion 811A generates the frictional heat between the distal end portion 818 and the target site. Then, the target site is incised while coagulating. As described above, the ultrasound treatment tool 2A according to the present embodiment also functions as a monopolar treatment tool.

Even when the ultrasound treatment tool 2A according to the present embodiment described above is adopted, the same effects as those of the exemplary embodiment described above are obtained.

OTHER EMBODIMENTS

Although the embodiments for carrying out the disclosure have been described so far, the disclosure should not be limited only by the exemplary embodiments and modifications described above.

Although end portions 833 to 835 are formed by molding the mold portions 83 and 83A in the embodiments and modifications described above, the disclosure is not limited thereto. For example, after the mold portions 83 and 83A are molded, the end portions 833 to 835 may be formed by performing chamfering processing such as C chamfering or R chamfering.

In the embodiments and modifications described above, both the ultrasound energy and the high frequency energy are applied to the target site, but the disclosure is not limited thereto, and only the ultrasound energy is applied to the target site. In addition, at least one of the high frequency energy and the heat energy from the heater or the like and ultrasound energy may be applied to the target site.

According to the ultrasound probe and the ultrasound treatment tool according to the disclosure, it is possible to prevent the occurrence of clogging of the biological tissue while avoiding the unintended action on the biological tissue.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing an ultrasound probe, comprising:
    forming an elongate probe body that extends along a central axis from a proximal end to a distal end and is configured to transmit ultrasound vibration from the proximal end to the distal end;
    forming a coating portion by applying a liquid containing a resin component as a main component and a filler to a predetermined region on an outer surface of the probe body and heating the liquid; and
    forming a mold portion by placing the probe body on which the coating portion is formed in a die and pouring a resin containing the resin component serving as the main component of the coating portion in the die, wherein:
    the mold portion includes an end on a distal end side of the mold portion along the central axis,
    the end of the mold portion includes an inclined surface such that a thickness of the end of the mold portion decreases in a distal direction along the central axis, and
    the coating portion is formed from a resin such that a coefficient of linear expansion of the coating portion is greater than a coefficient of linear expansion of the probe body and less than a coefficient of linear expansion of the mold portion.

2. The method according to claim 1, further comprising:
    performing a surface treatment on the outer surface of the probe body to increase surface roughness of the outer surface of the probe body prior to applying the liquid to the predetermined region.

3. The method according to claim 1, wherein the mold portion is integrally molded on the coating portion.

4. The method according to claim 1, wherein the mold portion and the coating portion are provided on an identical region on the probe body.

5. The method according to claim 1, wherein the resin component serving as the main component is polyether ether ketone (PEEK).

6. The method according to claim 1, wherein the coating portion contains mica as the filler.

7. The method according to claim 1, wherein the mold portion contains a resin containing the resin component serving as the main component of the coating portion and a glass filler.

8. The method according to claim 1, wherein the mold portion is formed with an annular portion extending around an entire circumference of the probe body.

9. The method according to claim 1, wherein the coating portion and the mold portion have a lower thermal conductivity than the probe body.

10. The method according to claim 1, wherein the mold portion is formed such that the resin component of the mold portion is fused to the resin component of the coating portion.

* * * * *